United States Patent [19]

Morgan et al.

[11] Patent Number: 5,223,260
[45] Date of Patent: Jun. 29, 1993

[54] FLAVORING, FRAGRANCE, SKIN TEXTURIZING AND DEODORANT MATERIALS AND METHOD OF MAKING SAME

[75] Inventors: Robert D. Morgan; Peter A. Blagdon, both of Paris, Ill.

[73] Assignee: Morgan Food Products, Inc., Paris, Ill.

[21] Appl. No.: 297,402

[22] Filed: Jan. 17, 1989

[51] Int. Cl.$^5$ .............................................. A61K 7/02
[52] U.S. Cl. ...................... 424/439; 424/69; 424/76.1; 426/312; 426/471; 514/772; 264/12
[58] Field of Search ............... 426/312, 471; 424/439, 424/76.1, 440, 69; 264/12; 23/313; 514/772

[56] References Cited

U.S. PATENT DOCUMENTS

| | | | |
|---|---|---|---|
| 2,020,719 | 11/1935 | Bottoms | 264/12 |
| 2,785,983 | 3/1957 | McMath | 99/140 |
| 2,857,281 | 10/1958 | Schultz et al. | 99/140 |
| 3,161,602 | 12/1964 | Herbig et al. | 22/316 |
| 3,202,731 | 8/1965 | Grevenstuk et al. | 264/12 |
| 3,423,489 | 1/1969 | Arens et al. | 264/4 |
| 3,436,355 | 4/1969 | Bakan | 252/316 |
| 3,615,723 | 10/1971 | Meade | 426/471 |
| 3,764,346 | 10/1973 | Noznick et al. | 426/213 |
| 3,819,838 | 6/1974 | Smith et al. | 426/89 |
| 3,856,699 | 12/1974 | Miyano et al. | 252/316 |
| 3,949,096 | 4/1976 | Johnson et al. | 426/471 |
| 3,977,992 | 8/1976 | Hofacker | 252/316 |
| 4,173,492 | 11/1979 | Pollard | 106/316 |
| 4,675,236 | 6/1987 | Ohkawara et al. | 428/498 |
| 4,702,925 | 10/1987 | Verrico | 426/471 |

OTHER PUBLICATIONS

Kirk-Othmer Encyclopedia of Chemical Technology, 3d ed., vol. 15 John Wiley & Sons, pp. 473-474.

*Primary Examiner*—Thurman K. Page
*Assistant Examiner*—Amy Hulina
*Attorney, Agent, or Firm*—Roper & Quigg

[57] ABSTRACT

Flavorings, seasonings, fragrances, skin texturizers, deodorants, and the like, and methods of making such are disclosed. The method includes melting a water soluble carrier material and dispersing an additive within the melt. The dispersed melt is then sprayed into a chilled gas and the resulting powder is recovered.

10 Claims, 1 Drawing Sheet

FLAVORING, FRAGRANCE, SKIN TEXTURIZING AND DEODORANT MATERIALS AND METHOD OF MAKING SAME

FIELD OF THE INVENTION

This invention relates to compositions of flavorings, seasonings, fragrances, skin texturizers, deodorants and the like and to methods of preparing such compositions.

DESCRIPTION OF THE PRIOR ART

Many compositions have heretofore been proposed for use as flavoring, seasoning, fragrance, skin texturizing, or deodorant materials, and the like, and methods have been disclosed for the production thereof.

For example, U.S. Pat. No. 2,857,281, issued to Schultz, et al., described a process of forming a hot, liquid emulsion of a volatile flavoring agent, such as citrus oil, in a sugar base, preferably a non-crystallizing mixture of at least two different sugars and a minor amount of water. The flavoring agent is added to the hot, liquid sugar solution at temperatures of about 80° C. to 150° C. (Schultz et al., col. 9, lines 44-49), i.e., from about 176° F. to 302° F. The hot, liquid emulsion is then forced through an orifice into a low humidity atmosphere at such a rate so that the emulsion issues from the orifice as a stream of droplets. The stream preferably is allowed to fall about ½ to 8 inches and, while the droplets are still in a plastic condition, then allowed to impinge on a solid surface. As the droplets impinge on the solid surface, they form globular particles. (Schultz et al., col. 2, line 10—col. 4, line 35).

U.S. Pat. No. 2,785,983, issued to McMath, discloses a process for making a flavoring material by spray-cooling a uniform solution of the active flavoring ingredient in a melted edible hard fat or hydrogenated glyceride oil to form a dry solid particulate flavoring material. These particulate flavoring materials have a melting point of at least 115° F. and preferably 125° F. or above. (McMath, col. 2, lines 35-66). The use of a hard fat or hydrogenated glyceride oil, as described by McMath, results in a flavoring material that is not water soluble.

U.S. Pat. No. 4,173,492, issued to Pollard, discloses a process for producing flakes of coated pigments for dry compounding with polymeric plastics or rubber materials. The color pigments are encapsulated in a wax, such as hydroxystearate wax. (Pollard, col. 6, lines 12-23). Such wax is non-water soluble.

U.S. Pat. No. 4,675,236, issued to Ohkawara, et al., describes a process for coating mono-core type microcapsules with waxes. The mono-core type material is formed, as by spray drying or pulverizing lump material. The core materials are then immersed in a wax solution, followed by vacuum drying. The resulting material (referred to as a "capsule-product") is then supplied together with air or nitrogen gas into a melting and cooling chamber. The chamber contains different temperature zones; the hot gas zone is generally higher than the melting point of the wax by 30°-200° C. The particles then fall into a cooling portion of the chamber wherein the temperature is below the melting point of the wax by 10°-200° C., and more preferably below by 50°-100° C. In this way, Ohkawara, et al.. indicate that the final product has a membrane with a highly smooth surface and a shape profiling the surface layer of the underlying core particle. (Ohkawara, et al., col. 2, line 60-69—col. 3, lines 1-55).

U.S. Pat. No. 3,856,699, issued to Miyano, et al.. describes a process for producing capsules having walls of a waxy material. The process comprises the dropwise dispersion of a waxy material containing a core material in an agitated aqueous medium at a temperature higher than the melting point of the waxy material, followed by passing the waxy material into a non-agitated aqueous medium at a temperature lower than the melting point of the waxy material. (Miyano, et al.. col. 1, lines 36-42, col. 2, lines 7-64).

U.S. Pat. No. 3,819,838, issued to Smith, et al., describes a granular or powdery solid composition comprising multiple capsules, each consisting of at least one primary capsule, wherein an active ingredient is encapsulated by a water soluble solid encapsulating material, which primary capsule is re-encapsulated in a water insoluble solid encapsulating material. (Smith, et al., col. 1, lines 59-65). Smith, et al., specifically note that water soluble encapsulated materials, as described in the prior art, are disadvantageous when mixed with other food ingredients, including water or moist ingredients. (Smith, et al.. col. 1, lines 41-58).

U.S. Pat. No. 3,764,346, issued to Noznick, et al., discloses the production of spray dried materials which may be used as a flavor enhancer.

Each of the representative prior art patents, discussed briefly above, has inherent disadvantages in relation to the production of the materials of the present invention. For example, the Noznick, et al., patent typifies the spray drying art. In this regard, in conventional spray drying technology, a material such as a flavor or fragrance additive material is incorporated into a carrier, such as water, a sugar solution, a fat emulsion, and the like. During spray drying operations, it is desired to vaporize or flash-off substantial amounts of the carrier material in order to leave a solid, powdery composition that includes the additive. However, in such typical spray drying operations, the temperature required to vaporize or flash-off the carrier is sufficiently high so as to volatilize significant amounts of the additive. Consequently, commensurately more additive must be included within the original material prior to spray drying in order to retain the characteristics, such as flavor or fragrance, desired of the final product. If such is not done, it is necessary to utilize more of the final spray dried material to provide the desired level of flavoring or fragrance for ultimate use.

Likewise, prior art represented by, for example, Pollard, U.S. Pat. No. 4,173,492, includes not only a high operating temperature, i.e., substantially above the boiling point of water, but also results in a material coated with a fat or wax. As such, the composition is non-water soluble.

BACKGROUND OF THE INVENTION

The above-noted prior art patents demonstrate that there are various methods in existence to provide a coated material having flavoring or fragrance characteristics. However, each of these methods provides distinct disadvantages. The methods require relatively high operating temperatures which will typically cause significant amounts of the additive to volatilize during production. In addition, several of the methods require the use of a fat or wax substance thereby rendering the final product insoluble in water.

The above-noted disadvantages, and others routinely encountered in the art, are overcome in the practice of the present invention.

Thus, it is an object of the present invention to overcome these disadvantages by providing a method to produce flavoring, fragrance, texturizing, or deodorant materials which are water soluble and which have an enhanced flavor, fragrance, texturizing, or deodorant characteristic.

It is a further object of the present invention to provide a method of producing such materials at temperatures sufficiently low so as to assure minimal volatilization of the additive components during production.

It is yet another object of the present invention to provide a method to produce such a material that is more economical in comparison to the prior art methods.

These and other advantages of the present invention will become apparent to one skilled in the art with reference to the attached drawing and the following description of the preferred embodiment.

DESCRIPTION OF THE PREFERRED EMBODIMENT

Figure 1:
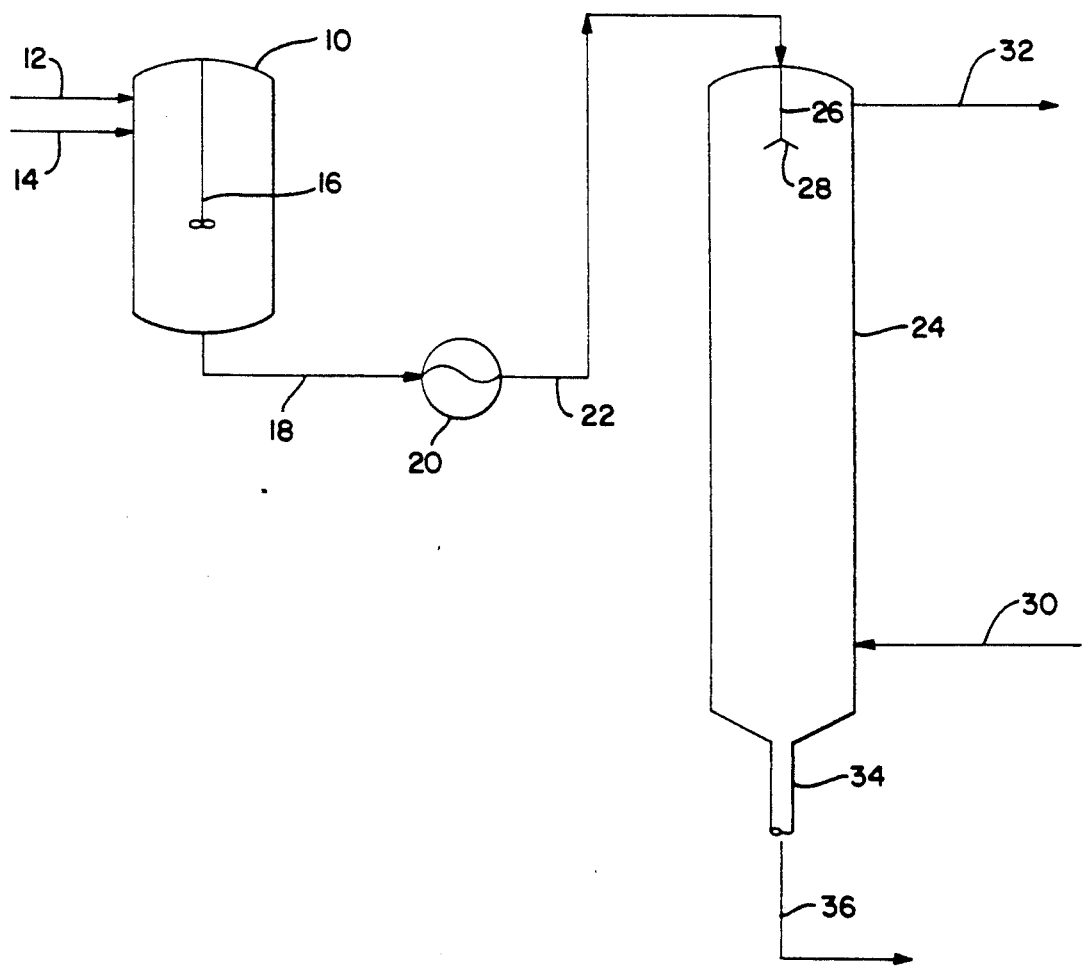
FIG. 1 is a schematic of an apparatus useful in performing the method of the present invention.

The apparatus useful in the method of the present invention to prepare the novel compositions of the present invention is schematically described in FIG. 1. As there shown, a mix tank 10 is provided. Inlet lines 12 and 14 feed into mix tank 10, with inlet line 12, which may be equipped with a metering device (not shown), used to flow a water soluble, low melting point carrier material into mix tank 10. Inlet line 14, which may be equipped with a metering device (not shown), is used to feed the desired flavor or fragrance component into mix tank 10. Mix tank 10 is provided with motorized stirrer 16, which may be of the high speed variety, that acts to ensure that the carrier material and the additive component (which may be, for example, a flavoring, seasoning, fragrance, texturizing additive, and the like) are intimately mixed. Mix tank 10 may also be provided with one or more heater elements (not shown) located either in or surrounding the tank to allow the internal temperature of the tank to be regulated. Such construction is advantageous when the melting point of the carrier material is greater than ambient temperature. Alternatively, the carrier material and the additive component may be pre-mixed in a pre-mix tank (not shown). In such a circumstance, the mix tank 10 advantageously may be used as an interim storage tank to assure that the carrier material and the additive component are intimately mixed prior to use.

Mix tank 10 is provided with an outlet line 18 feeding high pressure pump 20. The high pressure pump 20 is connected to spray tank 24 via line 22. The spray tank 24 is equipped with a spray nozzle 28 having a plurality of openings therein, as is conventional in the spraying art. The spray nozzle 28 may be offset from the entry point to the spray tank 24 via extension line 26.

The spray tank 24 has at one end thereof an inlet line 30 for flowing a gas, such as for example, air, carbon dioxide, nitrogen, and the like, into the spray tank 24. In practice, it is advantageous to insulate the line 30. At the other end of the spray tank 24, an outlet line 32 is provided for flowing gas from the spray tank 24. When the spray tank 24 is a vertical tank, it may also provided at the lowermost end thereof with an extension 34 to allow the product to be removed easily from the spray tank 24. The product is then flowed, such as through line 36, to mix tanks, storage tanks, or other product utilization areas.

In practicing the method of the present invention, it is preferred that the temperature of the gas flowing through inlet line 30 into spray tank 24 be about 60° F. or less. This may be accomplished by passing the gas through a conventional chiller or heat exchange unit prior to introduction into the spray tank 24 and may also be accomplished by providing an expansion nozzle in communication with the inlet line 30 and the spray tank 24. However accomplished, the "chilled" gas entering spray tank 24 flows from the area generally surrounding inlet line 30 in an upward direction to outlet line 32. Because the temperature of the gas flowing through outlet line 32 is about 75° F., it will be appreciated that the spray tank 24 has a temperature gradient from the top thereof to the bottom portion thereof.

As previously mentioned, the mix tank 10 is utilized to mix the carrier material with the additive component. It has been discovered that the carrier material can be selected from the general classes of substances comprising alcohols, aldehydes, ketones, esters, and fatty acids, provided that such materials are water soluble and have relatively low melting points, i.e., from about 115° F. to about 190° F. The low melting point of the carrier material ensures that it can be mixed with the additive component without significant loss of that component through evaporation or volatilization.

As the molten mixture of the carrier material and the additive component is sprayed from the spray nozzle 28 in the mix tank 24, there will be little additional evaporation or volatilization of the additive component. This occurs because the temperature of the chilled gas entering the spray tank 24 through inlet line 30 is maintained below the volatilization temperature of such component. Consequently, when the molten mixture is sprayed through spray nozzle 28 and falls, via gravity, to the lower portion of spray tank 24, the temperature of the mixture is lowered below the melting point of the carrier material and small, solid powdery particles are formed. These powdery particles encapsulate, or carry therewith, the additive component. It will be appreciated that as the mixture falls through the spray tank 24, the upwardly flowing gas is warmed. It has been observed that gas exiting the outlet line 32 has a temperature in the range of about 70°-90° F., depending on the temperature of the carrier material and the temperature of the gas in inlet line 30. In addition, as one skilled in the art will appreciate, the size of the powdery particles formed depends on the orifice size of the nozzle 28, the velocity of the gas flowing from the inlet line 30 through the outlet line 32, and the length of "fall" in the spray tank 28, among others. In this regard, a commercially available number 15 nozzle and a length of "fall" of 6 to 36 feet have been found to be useful in the method of the present invention, although other nozzle sizes and "fall" lengths can be effectively utilized.

Although the spray tank 24 depicted in FIG. 1 is shown as a vertical tank with the gas from inlet line 30 flowing countercurrent to the direction of travel of the carrier material exiting the spray nozzle 28, the line 32 could be used as the inlet line for the chilled gas. In this configuration, the outlet line for the gas could be line 30, or another line (not shown) connected to the tank 28. In such a situation, the chilled gas would flow cocurrent to the carrier material. Alternatively the countercurrent or cocurrent flow of chilled gas could also apply to a horizontally positioned spray tank, with the product falling into a trough, moving bed, or the like. As a further alternative, the chilled gas may be flowed cross-current to the direction of travel of the carrier material.

As a further description of the carrier materials useful in the present invention, it is preferred that the materials have the following properties:

1. Normally solid at room temperature;
2. Melting point between about 115° and about 190° F.;
3. Soluble or dispersible in water at temperatures from about 35° F. to about 212° F.;
4. Non-toxic to humans and animals if ingested;
5. Non-harmful to humans and animals upon skin or eye contact.

Representative carrier materials which have the foregoing properties include polyethylene glycol; block polyols (i.e.. polyoxyalkene glycols) having an average molecular weight above about 4000 and preferably between about 8000 and about 15000; fatty alcohol ethylene oxide ethers having a relatively high percent of ethylene oxide, such as cetyl alcohol, lauryl alcohol, and stearyl alcohol.

Non-limiting examples of representative additive components include lemon oil, orange oil, oleoresin capsicum, basil oil, ginger oil, lavender oil, rose oil, peppermint oil, baby oil, and the like.

A further description of the present invention is set forth in the following Examples.

EXAMPLE 1

In order to establish the utility of the present invention, 1800 grams of polyethylene glycol (average molecular weight of about 3350) was melted (melting point 127° F.) and 200 grams of a commercially available 100% lemon oil flavorant (comprised of natural and artificial lemon oil) was mixed into the melt. As a simple test to determine if the mixture could be sprayed, a small amount of the mixture was dropped onto a cold metal plate (temperature at about 62° F). The mixture solidified readily.

The mixture, while still in the melt state, was then sprayed using the apparatus as depicted in FIG. 1. The mixture sprayed readily with no clogging of the nozzle orifices. A free flowing, fine powder was formed upon spraying. The powder dissolved readily in water (water temperature about 55° to 60° F.).

19 grams of granulated sugar, 1.5 grams of citric acid and 1.5 grams of the powder made above was mixed into 100 grams of 35° F. tap water. The resulting beverage had a distinct "fresh" lemon flavor and due to the Tindall effect of the tiny droplets of lemon oil was slightly turbid, giving a cloudy effect similar to lemonade.

EXAMPLE 2

1400 grams of polyethylene glycol (average molecular weight of 8000 was melted (melting point 141° F.) and 600 grams of a commercially available 100% orange oil was, with vigorous stirring, mixed into the melt. When dropped onto a cold metal plate, as described in Example 1, the melt solidified readily. The melt was then sprayed, as in Example 1, and a free flowing, fine powder was formed. The powder had a strong orange aroma and taste and was readily soluble in water (water temperature about 55° to 60° F).

19 grams of granulated sugar, 1.5 grams citric acid and 0.5 grams of the above powder were mixed with 100 grams of 55° F. tap water. The mixture dissolved readily giving an orange flavored beverage with some turbidity due to suspended orange oil droplets. The dispersion was observed for 2 hours and showed no sign of oil separation, indicating a stable emulsion.

EXAMPLE 3

1800 grams of the polyethylene glycol used in Example 2 was melted. 200 grams of a commercially available baby oil was, with vigorous stirring, mixed into the melt. The melt was then sprayed, as in Example 1, and a tacky powder was formed. One weight percent of amorphous calcium silicate was dry blended with the powder and the powder then became free flowing.

10 grams of the above powder was mixed with 90 grams of commercially available dry hand cleaning soap. The resulting material, when used as a soap, left the hands feeling soft and less raw than when the original cleaning soap was used alone. From this, it was concluded that the sprayed powder could be used in, for example, dry bath soap and salts to provide a baby oil carrier for skin moisturizing and texturizing purposes due to the emollient characteristic of the baby oil.

EXAMPLE 4

1600 grams of the polyethylene glycol used in Example 2 was melted and 400 grams of oleoresin capsicum (1,000,000 Scoville units) was stirred into the melt. The resulting mixture crystallized when dropped onto a cold metal plate, as described in Example 1. The melt was then sprayed, as in Example 1, and a free flowing, fine red orange powder was formed. The powder had a strong red pepper aroma and a very "hot" taste. From this, it was concluded that the powder could be used to provide a red pepper flavoring.

EXAMPLE 5

1600 grams of the polyethylene glycol used in Example 2 was melted and 400 grams of a commercially available 100% synthetic oil of cinnamon was stirred into the melt. When dropped onto a cold metal plate, as described in Example 1, the melt crystallized readily. The melt was then sprayed, as in Example 1, and a free flowing, fine powder was formed. The powder had a strong cinnamon aroma and taste. From this, it was concluded that the powder could be used to provide a cinnamon flavoring.

EXAMPLE 6

1600 grams of the polyethylene glycol used in Example 2 was melted and 400 grams of a commercially available 100% geraniol (a rose-geranium synthetic fragrance component) was stirred into the melt. When dropped onto a cold metal plate, as described in Example 1, the melt crystallized rapidly. The melt was then sprayed, as in Example 1, and a free flowing, fine powder was formed. The powder had a pleasant rose-geranium fragrance. The powder readily dissolved in water (water temperature about 85° F.) and provided a pleasant perfumed solution. From this, it was concluded that the powder could be used as a fragrance material.

EXAMPLE 7

200 pounds of the polyethylene glycol used in Example 2 was melted and 50 pounds of cold pressed orange oil was stirred into the melt (final melt temperature after stirring was about 163° F.). The melt was then sprayed, as in Example 1, through a commercially available number 15 nozzle at 750 PSIG into the spray tank 24 having a length of "fall" of 36 feet (temperature of gas in inlet line 30 was about 52° F.). A free flowing, fine powder was formed that was readily soluble in water.

EXAMPLE 8

1800 grams of a commercially available block polyol (polyoxyalkene glycol) having an average molecular weight of 14,600 and a melting point of 134° F. was melted and 200 grams of the commercially available lemon oil used in Example 1 was stirred into the melt. When dropped onto a cold metal plate, as described in Example 1 was stirred into the melt. The mixture, while then sprayed, as in Example 1, into the spray tank 24 having a temperature (prior to spraying) of about 44° F. A free flowing, fine powder was formed that dissolved readily in water at about 55° F.

EXAMPLE 9

1800 grams of the polyethylene glycol used in Example 1 was melted and 200 grams of the lemon oil used in Example 1 was stirred into the melt. The mixture, while still in the melt state, was sprayed, as in Example 1, into the spray tank (initial temperature of 57° F.) and a free flowing, fine powder was formed. 10 grams of the thus formed powder was dry mixed with 500 grams of a commercially available unscented oil-dry. The mixture had little to no apparent odor. A sample of the resulting mixture was taken and 20 ml of room temperature water (used to simulate cat urine) was poured over the mixture. A very apparent lemon oil odor was released. From this it was concluded that the powder could be used in applications where an odorant/deodorant was desired, such as for example in cat litter boxes, animal kennels, and others.

EXAMPLE 10

800 grams of the polyethylene glycol used in Example 1 was melted and 200 grams of the lemon oil used in Example 1 was mixed into the melt. When dropped onto a cold metal plate, as described in Example 1, the melt solidified slowly. The melt was then sprayed but the pump failed. Therefore, this run was terminated.

EXAMPLE 11

800 grams of the polyethylene glycol used in Example 1 was melted and 200 grams of a commercially available chocolate flavorant dissolved in propylene glycol was stirred into the melt. When dropped onto a cold metal plate, as described in Example 1, the melt had a taffy-like amorphous consistency, but did not solidify. It was concluded that the composition of the melt in this specific Example would not spray adequately.

EXAMPLE 12

1600 grams of the polyethylene glycol used in Example 2 was melted and 400 grams of a commercially available chocolate flavorant dissolved in propylene glycol was stirred into the melt. When dropped onto a cold metal plate, as described in Example 1, the melt had a taffy-like amorphous consistency, but did not solidify. It was concluded that the composition of the melt in this specific Example would not spray adequately.

EXAMPLE 13

1 gram of commercially available Red Dye No. 3 was dissolved in 100 grams of water. 1900 grams of the polyethylene glycol used in Example 2 was melted and 100 grams of the dye solution was mixed into the melt. The mixture was a brilliant red but had an amorphous character and would not solidify when dropped onto a cold metal plate as described in Example 1. It was concluded that the composition of the melt in this specific Example would not spray adequately.

We claim:

1. An encapsulated flavorant material, consisting essentially of from about 70 to about 90 weight percent of a water soluble, edible carrier material selected from the group consisting of polyethylene glycol and polyoxyalkene glycols having an average molecular weight of between about 4,000 and about 15,000, and from about 30 to about 10 weight percent of a flavorant dispersed in said carrier material, wherein said flavorant material is characterized as a free flowing powder formed at a temperature below the melting temperature of said carrier material.

2. A method of manufacturing an encapsulated flavorant material consisting essentially of the steps of:
   a. melting a water soluble, edible carrier material selected from the group consisting of polyethylene glycol and polyoxyalkene glycols having an average molecular weight of between about 4,000 and about 15,000, which carrier is solid at room temperature;
   b. dispersing within the melted carrier, formed in step a, a flavorant to produce a dispersed melt;
   c. transporting said dispersed melt to a nozzle positioned within a chamber and spraying said dispersed melt through said nozzle, said chamber being cooled by flowing a non-reactive gas therethrough, the temperature of said gas, as said gas enters said chamber, being less than the melting temperature of said carrier;
   d. solidifying said dispersed melt by contacting said dispersed melt with said gas flowing through said chamber; and
   e. recovering the solid flavorant material formed by step d.

3. The method of claim 1, further including the step of mixing said solid flavorant with a drying agent to reduce the tackiness of said solid flavorant.

4. The method of claim 2, wherein the melting point of said carrier is between about 115° F. and about 190° F.

5. The method of claim 2, wherein the temperature of said gas is initially about 60° F.

6. The method of claim 2, wherein said dispersed melt contacts said flowing gas through a distance of between about 6 and about 36 feet.

7. The method of claim 3, wherein said drying agent is calcium silicate.

8. A method of manufacturing an encapsulated flavorant material consisting essentially of the steps of:
   a. melting a water soluble, edible carrier material selected from the group consisting of polyethylene glycol and polyoxyalkene glycols having an average molecular weight of between about 4,000 and about 15,000, which carrier is solid at room temperature and has a melting point of between about 115° F. and about 190° F.;

b. dispersing within the melted carrier, formed in step a, a flavorant to produce a dispersed melt;

c. transporting said dispersed melt to a nozzle positioned within a chamber and spraying said dispersed melt through said nozzle, said chamber being cooled by flowing a non-reactive gas therethrough, the temperature of said gas, as said gas enters said chamber, being initially about 60° F.;

d. solidifying said dispersed melt by contacting said dispersed melt with said gas, flowing through said chamber, through a distance of between about 6 and about 36 feet; and e. recovering the solid encapsulated flavorant material formed by step d.

9. The method of claim 8, further including the step of mixing said solid flavorant with a drying agent to reduce the tackiness of said solid flavorant.

10. The method of claim 9, wherein said drying agent is calcium silicate.

* * * * *